US005833924A

United States Patent [19]
McClintock et al.

[11] Patent Number: 5,833,924
[45] Date of Patent: Nov. 10, 1998

[54] SAMPLING-ASSAY DEVICE AND INTERFACE SYSTEM

[75] Inventors: Joseph McClintock; Mary Ann Childs, both of Baltimore; David Bernstein, Elderburg, all of Md.

[73] Assignee: Universal Healthwatch, Inc., Columbia, Md.

[21] Appl. No.: 580,096

[22] Filed: Dec. 22, 1995

[51] Int. Cl.$^6$ .................................................... G01N 21/64
[52] U.S. Cl. ......................... 422/58; 422/82.08; 436/528
[58] Field of Search ................................ 422/52, 56, 58, 422/82.08, 82.09; 436/532, 535, 164, 165, 169, 172, 805, 524, 528, 531

[56] References Cited

U.S. PATENT DOCUMENTS

| | | |
|---|---|---|
| 1,967,557 | 7/1934 | John . |
| 4,225,557 | 9/1980 | Hartl et al. . |
| 4,250,257 | 2/1981 | Lee et al. . |
| 4,385,113 | 5/1983 | Schreoder et al. . |
| 4,396,579 | 8/1983 | Schreoder et al. . |
| 4,719,182 | 1/1988 | Burdick et al. . |
| 4,774,192 | 9/1988 | Terminello et al. . |
| 4,803,170 | 2/1989 | Stanton et al. . |
| 4,826,772 | 5/1989 | Meathrel . |
| 4,833,088 | 5/1989 | DeSimone et al. . |
| 4,857,453 | 8/1989 | Ullman et al. ............................. 422/58 |
| 4,861,711 | 8/1989 | Friesen et al. . |
| 4,863,689 | 9/1989 | Leong et al. . |
| 4,952,373 | 8/1990 | Sugarman et al. ....................... 436/165 |
| 4,981,653 | 1/1991 | Marino . |
| 5,030,558 | 7/1991 | Litman et al. ............................. 422/58 |
| 5,037,614 | 8/1991 | Makita et al. . |
| 5,075,078 | 12/1991 | Osikowicz et al. ....................... 422/56 |

(List continued on next page.)

FOREIGN PATENT DOCUMENTS

88/08534   11/1988   WIPO .

OTHER PUBLICATIONS

M. DeLuca, et al., Factors Affecting the Kinetics of Light Emission from Crude and Purified Firefly Luciferase, Analytical Biochem, 95:194–98 (1979).

I. Johnson, Optical Properties of Fluorescent Probes, Part I, pp. 1–4, Molecular Probes, Inc.

Phycobiliproteins and their Conjugates, Set 14, pp. 77–79, Molecular Probes, Inc.

Hamamatsu Photonics K.K., Photosensor Modules H5773/H5783/H5784 Series, Technical Data (Jan. 1995).

Instruments, Test & Measuring, Keithley Electrometers, Picoammeters and Voltmeters Data (1993).

Solid State Lamps, Model 4304H6 & 4304S, Industrial Devices.

*Primary Examiner*—Jeffrey Snay
*Attorney, Agent, or Firm*—Foley & Lardner

[57] ABSTRACT

A system and method for detecting a target analyte includes a sampling device, a holder, a light source, a light detector, and a quantifier (ammeter). The device has reading and sampling portions connected by a transfer portion. The holder has a housing, including a tray, which has a compartment adapted to seat the sampling device and an opening extending therethrough, slidable therein. The sampling portion is aligned with the tray opening when it is seated. When the tray is closed, the tray opening is aligned with the light detector and the light source. Once the sampling portion is exposed to a sample, carrier liquid is introduced to the sampling portion. While the carrier travel to the reading portion, the target analyte picks-up a labeling luminescent agent contained in the transfer portion. The reading portion captures the labeled target analyte. The non-captured elements exits the reading portion, leaving only the target analyte bound to the luminescent agent, which glows when exposed to light. To quantify the emitted light, the sampled device is seated into the tray and moved into the holder, whereupon the reading portion is exposed to the light source. The light detector reads the light emitted by the sample and generates a signal. This signal is then converted to quantifiable data indicative of the target analyte quantity, using for example, an ammeter.

18 Claims, 3 Drawing Sheets

U.S. PATENT DOCUMENTS

| | | |
|---|---|---|
| 5,188,965 | 2/1993 | Wannlund . |
| 5,188,966 | 2/1993 | Eikmeier et al. . |
| 5,207,984 | 5/1993 | Kheiri . |
| 5,234,813 | 8/1993 | McGeehan et al. . |
| 5,281,395 | 1/1994 | Markart et al. ............................ 422/58 |
| 5,284,622 | 2/1994 | Krause et al. . |
| 5,290,513 | 3/1994 | Berthold et al. .......................... 422/52 |
| 5,302,348 | 4/1994 | Cusack et al. ....................... 422/82.09 |
| 5,354,692 | 10/1994 | Yang et al. . |
| 5,356,782 | 10/1994 | Moorman et al. . |
| 5,366,867 | 11/1994 | Kawakami et al. . |
| 5,384,264 | 1/1995 | Chen et al. . |
| 5,435,970 | 7/1995 | Mamenta et al. . |
| 5,441,698 | 8/1995 | Norell . |
| 5,504,013 | 4/1996 | Senior ..................................... 436/165 |
| 5,563,042 | 10/1996 | Phillips et al. ............................ 422/58 |

SAMPLING-ASSAY DEVICE AND INTERFACE SYSTEM

BACKGROUND

The ability to detect bacterial contamination is paramount to improving food safety. During food processing, food can become contaminated with bacteria and spoil. Food poisoning can result if food contaminated with pathogenic bacteria, or its toxic products, is ingested without proper cooking.

Standard culture plate methods for monitoring surfaces for bacterial contamination require a sterile sample collection device (generally a swab or sponge) and suitable culture media, which after inoculation, must be incubated at a controlled temperature for a minimum of several hours to days. These methods are too cumbersome and time consuming, especially if used by untrained workers. Rapid bacteria tests need to be implemented in slaughterhouses and food handling establishments to improve safety. In these establishments, one must rapidly determine whether additional cleaning is required or whether proper safety procedures have been followed. To do that, a quick, reliable bacteria measurement is needed. Unfortunately, this is often not possible because present methods require several hours or even days by trained laboratory technicians or require elaborate testing equipments that are not readily transportable to on site locations.

Attempts have been made to overcome these shortcomings with more sensitive chemiluminescence detection methods. One such chemiluminescence method measures adenosine triphosphate (ATP) to indirectly measure the bacteria content. This detection is reliable because all bacteria contain some ATP. Chemical bond energy from ATP is utilized in the chemiluminescent reaction occurring, for example, in the tails of the firefly *Photinus pyralis*. The mechanism of this chemiluminescence reaction has been well characterized (DeLuca, M., et al, 1979 Anal. Biochem. 95:194–198). The components of this reaction can be isolated free of ATP and subsequently used to detect ATP in other sources by a reaction that begins with formation of an enzyme bound luciferyl-adenylate complex and free inorganic pyrophosphate and ends with a rapid reaction of this complex with molecular oxygen to produce light, $CO_2$, and adenosine monophosphate (AMP).

One conventional light measuring method involves counting photons with a light measuring instrument. Photographic films also have been used to monitor chemiluminescent reactions, as described for example in U.S. Pat. No. 4,396,579. A drawback of these types are that they are complex and difficult to use.

Firefly luciferin-luciferase reactions have been used for detecting microorganisms, as described in U.S. Pat. Nos. 4,385,113 and 5,366,867. These methods, however, suffer a number of deficiencies. Lyophilized luciferase-luciferin reagent is unstable at room temperature during long term storage and is unstable after liquid reconstitution over short time intervals. Additionally, after reconstitution, the reagent solution emits significant amount of light even in the absence of ATP, which decreases detection sensitivity.

The reagent instability problem was partly addressed by drying luciferin-luciferase reagents separately onto plastic surfaces. But this required an additional step of transferring microorganisms from a collection device to a plastic surface, increasing complexity. Further, while this solves the instability problem, it unfortunately lowers the detection sensitivity and creates a new problem—incomplete ATP transfer from the collection device to a separate plastic surface containing the luciferase-luciferin reagent. Furthermore, this solution introduces a new time variable between the transfer and the light emission measurement.

Adding reagent at timed intervals causes additional problems because the light emission kinetics become shorter as the light intensity decreases. The twin timing and reagent instability problems also plague other chemiluminescence chemistries that have been developed to detect target analytes. For example, U.S. Pat. No. 4,396,579 describes a complicated, expensive automated machine designed to add chemiluminescent reagent at fixed time intervals to overcome the light emission kinetic problem. The reagent instability and the timing problems make this machine unusually complex.

Thus, there is a need for an assay device that benefits from high sensitivity and speed of chemiluminescence detection, but one that excludes the aforementioned complexity, timing, reagent instability, and high background light emission problems. Copending U.S. patent application Ser. No. 560/094, filed Nov. 17, 1995, hereafter "first copending application"), entitled CHEMILUMINESCENT ASSAY METHODS AND DEVICES FOR DETECTING TARGET ANALYTES, describes chemiluminescent assay methods and devices that fulfill this need. The disclosure of the first copending application is incorporated herein by reference.

The first copending application discloses a simple, easy to use chemiluminescent sampling assay device that eliminates or reduces the complexity associated with manually measuring and adding reagent at timed intervals. This sampling device also provides means to measure light intensity and allows rapid analysis of target analytes at the sample site. Specifically, it comprises a container or envelope holding a sampling strip having separate sampling and reagent portions. The reagent portion contains one or more dried chemiluminescent reagents. The device has a light-permeable portion that permits light generated by a chemiluminescent reaction within the sampling strip to exit the container. This sampling assay device eliminates or reduces much of the complexity associated with other known assay methods and, as a result, decreases the cost and training requirements for detecting target analytes. A wide range of target analytes can be detected by this device. In fact, the sampling portion of the device can collect virtually any type of target analyte containing ATP, not only from physical contact with a solid, but also from sample liquid applied or introduced thereto. The advantage of rapid and sensitive detection of bacteria can be realized through sensitive light detection using, for example, a photomultiplier. The first copending application discloses, in essence, a compact, self-contained assay device that allows light detection using any of known light detection methods, including an optical observation.

Notwithstanding the advantages and benefits of the ATP detection method described in the first copending application, the ATP detection method tests for presence of microorganisms, not a specific microorganism, since all microorganisms contain ATP. In this regard, it would be desirable to detect specific microorganisms. The present inventions provides such a capability.

Conventional instruments for measuring chemiluminescence, including luminometers and fluorometers, however, are not particularly suited for such an assay device that has a flat geometry. To this end, there is a need for a portable interface readily interfaceable with a photomultiplier or other known light detector to provide a simple, efficient light intensity reading from the sampling assay device of the type disclosed in the first copending application. Copending U.S. patent application Ser. No. 08/577,107, filed Dec. 22, 1995, (hereafter "second copending application"), entitled SAMPLING-ASSAY INTERFACE SYSTEM AND METHOD describes a system that fulfills this need, the disclosure of which is incorporated herein by reference.

Specifically, the second copending application describes a sampling-device holder interface system and a method for performing an assay for a target analyte from a sampling device of the type disclosed in the first copending application. The sampling system includes a sampling-device holder interface (hereafter "interface") and a quantifier for converting the output signal to quantifiable data indicative of the amount of the target analytes. Specifically, the interface comprises a sampling-device holder and a light detector—means for converting light generated from the sampling device to an output signal corresponding to the amount or intensity of the light generated—such as a photomultiplier or photodetector.

The interface holds a sampling device, which comprises a container and a sampling strip inside the container. The sampling strip has a sampling portion for introducing a sample, a reading portion containing a reagent for producing a chemiluminescent reaction with the target analytes, and a transfer portion connecting the sampling and reading portions for transferring the sample from the sampling portion to the reading portion. The container has an opening to permit introduction of samples to the sampling portion. It also has a light transmissive portion, such as a window or opening, visibly exposing the reading portion.

The holder includes a housing and a tray. The housing has at least first and second walls forming a cavity therebetween. One of the first and second walls has an opening or light transmissive window. The tray is received in the cavity and movable between opened and closed positions. The tray has a compartment adapted to seat and support the sampling assay device. The first opening is in registry with the reading portion when the tray is in the closed position to enable observation of the reading portion through the first opening. The light detector is connected to the housing, in registry with the first opening. The tray has a second opening extending through the compartment, which opening is in registry with the reading portion of the seated sampling device. When the tray is in the closed position, the second opening is in registry with the first opening to enable observation of the reading portion through both the first and second openings.

Not withstanding the advantages and benefits derived from the sampling device and the interface system adapted for the sampling device disclosed in the first and second copending applications, the interface system is not adapted for the luminescent (fluorescent or phosphorescent) light detection. Another potential drawback with this type of sampling device is that the chemiluminescent reaction takes place spontaneously as the chemiluminescent reagent mixes with the target analyte. In this regard, it is not possible to selectively take measurements or delay measurements once sampling is initiated. Hence, there is a need to selectively trigger luminescent reaction independently of sampling. The present inventions provides that capability.

SUMMARY

The present invention is drawn to a sampling device, an interface for holding the sampling device, and a system and method thereof for performing an assay for a target analyte from a sample.

According to the present invention, the sampling device comprises a sampling strip housed in a container. The sampling strip has a sampling portion for receiving a sample, a reading portion for emitting light, and a transfer portion connecting the sampling and reading portions for permitting transfer of the sample from the sampling portion to the reading portion. The reading portion contains an immobilized binding agent complementary to the target analyte. This enables the reading portion to capture or immobilize the target analyte within the reading portion while allowing non-captured elements to pass through or exit the reading portion. Specifically, the binding agent preferably is an antigen complementary to the target analyte.

One or both the sampling portion and the transfer strip contains a luminescent (fluorescent or phosphorescent) labeling agent, which glows when exposed to light. Preferably, the labeling agent, which preferably is chelated europium or europium compound, is contained within at least a portion of the transfer portion near or adjacent the reading portion. The labeling agent is bound to another binding agent complementary to the target analyte. Thus, the labeling agent specifically binds to the target analyte.

The container comprises a first layer and a second layer sandwiching the sampling strip and has means, which preferably is a first opening formed through the first layer and aligned with the sampling portion, to permit introduction of the sample to the sampling portion, and has a light transmissive portion exposing the reading portion. The light transmissive layer is preferably a second opening though the second layer and aligned with the reading portion. The second layer includes a light transmissive member to cover at least the second opening.

The sampling strip is made of materials that permit lateral flow of the sample in liquid, such as vibulous, adsorbent, or hydrophilic materials. But at least the reading portion is light transmissive. One light transmissive material meeting this requirement is a poly-carbonate membrane. The sampling strip further includes a collecting portion contiguous with the reading portion for absorbing excess liquid containing the labeling agent not captured along with the target analyte. In this regard, the collecting portion is formed of an absorbent material to wick away the excess liquid. If the entire length of the sampling strip is made of a polycarbonate membrane, the collection portion preferably has an absorbent layer provided over the polycarbonate membrane.

The sampling device preferably includes an adsorbent sample collecting member in contact with the sampling portion inside the container and aligned with the first opening.

The interface according to the present invention is adapted for use with the aforedefined sampling device. The interface comprises a sample holder, a light detector for converting light emitted from the sampling device to an output signal corresponding to the amount or intensity of the light generated, such as a photodetector or photomultiplier, connected to the holder and a light source, such as an LED, laser diode, or gas-filled lamp, connected to the holder. The holder comprises a housing having a first wall and a second wall. The first and second walls form a cavity therebetween, with the first wall having a first opening. A tray is received in the cavity and movable between an opened position and a closed position. The tray also has a compartment adapted to receive and support the sampling device and a second opening extending through the compartment. The second opening is in registry with the reading portion when the sampling device is seated in the compartment and in registry with the first openings to enable observation of the reading portion through the first and second openings.

The light detector has a light gathering window and is connected to the first wall so that the window is aligned with the first opening. The light source is aligned with the first opening and connected opposite the first opening. Specifically, the second wall has a third opening aligned with the first opening and the light source is seated in the third opening. The second wall is an enclosure having a channel and the first wall is a base plate connected to the enclosure, the channel defining the cavity.

When the tray is in the opened position, the tray blocks the first opening. The tray can also include a handle and is preferably slidable between the opened and closed positions. In this regard, the tray includes a pair of parallel slots, which are adapted to be occupied by fasteners spaced along the slots. The length of the slot less the spacing between the fasteners occupying the same slot defines the amount of the tray sliding movement.

A system according to the present invention is adapted for use with the aforedefined sampling device and includes the aforedefined interface, and further includes a quantifier, such as an ammeter, for converting the output signal from the light detector to quantifiable data indicative of the amount of the target analyte.

A method according to the present invention for performing an assay for a target analyte is adapted for use with the aforedefined sampling device. The sample suspected of containing the target analyte is exposed to the sampling portion. Then at least one carrier liquid is introduced to the sampling portion to move the target analyte to the reading portion. The moving carrier liquid containing the target analyte is labeled with a luminescent agent, such as chelated europium or europium compound, before the carrier liquid reaches the reading portion. The target analyte labeled with the labeling agent is bound or captured, using for example, an immobilized binding agent complementary with the target analyte, within the reading portion, while permitting non-captured elements to exit the reading portion. The reading portion now containing the captured analyte with the labeled agent is exposed to light. Then the light emitting from the reading portion is measured to detect presence of the target analyte.

The carrier liquid includes a target analyte extraction agent that extracts target analyte present in the sampling portion. According to the present invention, the reading of the captured analyte can be made at a later stage. In this regard, the sampled sampling device is seated onto a tray and inserted into a light-tight housing. The housing is provided with a light transmissive window to expose the reading portion and a light source for illuminating or charging the reading portion. If the luminescent labeling agent is fluorescent, then the light source is turned on continuously to charge the reading portion from one side, while a photodetector reads the amount of light emitted from the reading portion from the opposite side. If the luminescent labeling agent is phosphorescent, then the light source is selectively turned on and off. During the off phase, the reading portion is exposed to the photodetector. The output signal, which is indicative of the strength of light, is converted to quantifiable data indicative of the amount of the target analyte. For this purpose, an ammeter can be connected to the photodetector.

DETAILED DESCRIPTION OF THE DRAWINGS

Figure 1:
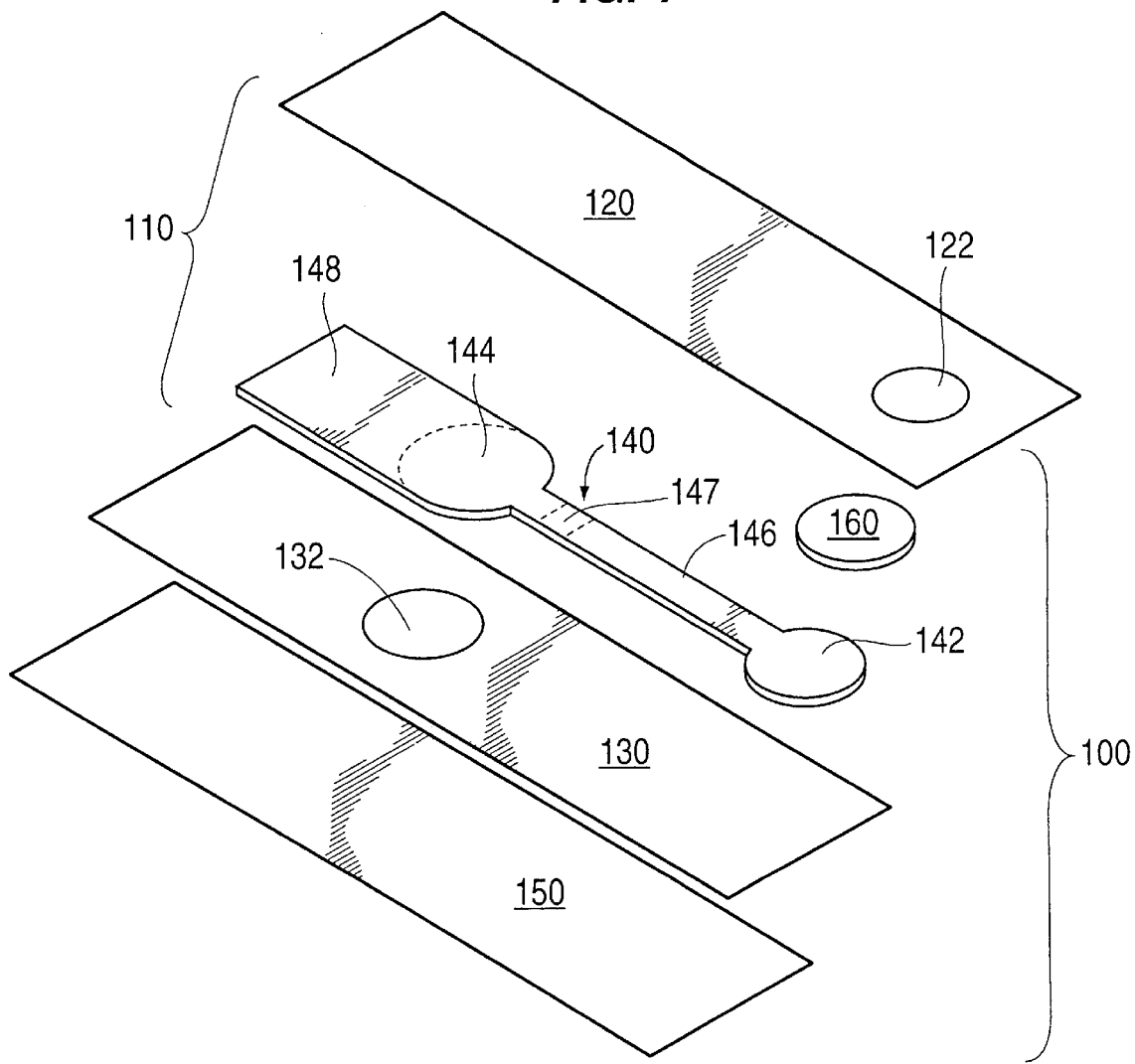
FIG. 1 is an exploded view of a sample assay device according to the present invention.

FIG. 1 illustrates a sampling assay device 100 according to the present invention, which device is particularly adapted for use with the interface 1 described herein. The device 100 includes a housing 110 for containing a sampling strip 140, which has a sampling portion 142 for receiving a sample, a reading portion 144 for emitting light, and a transfer portion 146 for transferring the sample to the reading portion. The housing 110 is defined by a top layer 120 and a bottom layer 130, each having an opening 122, 132 in alignment respectively with the sampling portion 142 and the reading portion 144.

Each of the top and bottom layers 120, 130 is preferably composed of a thin liquid impervious material, such as a plastic film. The sampling strip 140 is sandwiched and retained between the top and bottom layers 120, 130, which can be sealingly joined together, for example, by heat, adhesive, ultrasonic welds, or any physical means that retain layers together while containing the sampling strip therein. A single transparent film sheet can also be folded to form the upper and lower layers. Alternatively, a housing with three pre-sealed sides can also be used.

The bottom layer 130 preferably includes a sealing film 150 positioned underneath as shown in FIG. 1. This film 150 and the top layer 120 are preferably light transmissive (clear) to transmit light emitting from the reading portion. The film 150 and the top layer 120, however, could be structured so that only the regions directly below the bottom layer opening 132 and the region directly above the reading portion 144 are clear. Although FIGS. 1 and 3 show the film 150 positioned below the bottom layer, it can also be positioned above the bottom layer, below the sampling strip 140. The sealing film 150 can be omitted altogether if the bottom layer, at least the portion below and in registry with the reading portion 144, is formed of a clear material to provide a window for the reading portion. In this regard, the entire bottom and top layer could be made of a clear material if desired. Even just the opening 132 could be covered with a light transmissive material, from either above or below the bottom layer 130. The sampling portion 140 is positioned directly under the top-layer opening 122, sandwiched between the top layer 120 and the bottom layer 130.

An optional sample collecting member 160 is preferably sandwiched between the top layer 120 and the sampling portion 142, with the collecting member exposed to the top layer opening 122. The sampling portion is thus accessible through the envelope 110. The collecting member 160 is preferably adsorbent, which is preferably composed of fibrous material, such as glass fiber, cotton, dacron, or paper, and it may be porous, such as porous polyethylene or sintered glass.

The sampling strip 140 preferably is made of a material that permits lateral liquid flow, such as a vibulous, adsorbent, or hydrophilic membrane. At least the reading portion, however, is light transmissive so that it transmits light. A poly-carbonate membrane suits this requirement. The transfer portion 146 and the sampling portion 142 can be made of glass fiber for example. An ordinary skilled artisan will recognize many useful materials that permits lateral liquid flow and is light transmissive.

The sampling strip 140 also has a collecting portion 148 for absorbing excess liquid and sample components not immobilized in the reading portion 144. In this regard, the collecting portion preferably is made of an adsorbent or absorbent material such as paper, cellulose filter paper, etc. If the entire sampling strip is formed of the light transmissive material, such as a polycarbonate membrane, the collection portion 148 preferably includes an absorbent layer, such as cellulose paper to wick away excess liquid away from the reading portion.

The sampling and reading portions 142 and 144 are preferably wider than the transfer portion 146 connecting these wider portions, although many other configurations are possible. Although the sampling and reading portions are circular as shown, they can come in various other shapes, including rectangular, triangular, etc. The shape can be maximized for particular needs.

The sample collecting member 160, if used, is preferably in physical contact with the sampling portion 142 to maximize liquid transfer. The transfer portion 146 further has a labeling portion 147 adjacent or near by the reading portion. This labeling portion 147 contains a luminescent (fluorescent or phosphorescent) labeling agent, such as chelated europium or europium compound (phosphorescent) or phycobiliproteins (fluorescent) for labeling the analyte.

Specifically, the labeling portion 147 contains a conjugate (typically two molecules held together by one or more bonds) of a luminescent reporter molecule (agent) and a first binding agent that binds the target analyte. The luminescent agent can be either fluorescent such as, for example, fluorescein or a phycobiliprotein, or phosphorescent, such as a chelated europium or europium compounds. The "reporter molecule" for purposes of this invention can includes larger associations of molecules and atoms such as liposomes filled with fluors or enzymes, and particles such as gold or polystyrene coated with luminescent molecules.

The first binding agent binds to the target analyte in a solution. A preferred first binding agent is an antibody although other substances that can bind a particular antigen such as, for example, protein A (antibody antigen), lectin (glycolipid or glycoprotein antigen), streptavidin (antibody antigen), avidin (biotin target analyte), and hormore or trophic factor (cell surface receptor).

The first binding agent and luminescent reporter molecule are conjugated by any of a number of techniques known to an ordinary skilled artisan. In practice, the conjugate formed from a first binding agent and luminescent reporter molecule is placed into the labeling portion 147 by preparing a solution of the conjugate by spotting the solution onto labeling portion 147. The solution is then dried. Depending upon the composition of the labeling portion 147, however, it is preferred to include a carrier protein such as bovine serum album or milk in the solution to help prevent the conjugate from binding to the labeling portion 147. Detergent such as TWEEN-20 or TRITON X-100 can also be included to prevent non-specific binding of the conjugate to the labeling portion.

It is important to introduce detergent or other agent for releasing the target analyte or to releasing the labeling agent from the labeling portion before the labeling portion 147. Preferably, they are introduced with the carrier or buffer.

The labeling agent does not spontaneously react with the target analyte, but rather attaches thereto and glows when it is exposed to light. It thus needs to be triggered. This advantageously enables selective light measurement to be taken at anytime between 2 to 60 minutes after sampling.

As the sample in liquid, such as carrier liquid or buffer, travels toward the reading portion, it releases the labeling agent, which has a specific binding agent complementary to the target analyte. The labeling agent, however, will attach only to the target analyte. The carrier liquid now with the tagged or labeled target analyte (and any excess labeling agent not tagged with the target analyte) continues into the reading portion.

The reading portion 144 contains a second binding agent, which could be same as the first, such as an antibody or antigen complementary to the target analyte to capture the labeled analyte within the reading portion. This time, however, the second binding agent is bound to the light transmissive member, so that it does not flow out of the reading portion. Thus, the labeled analyte remains immobilized within the reading zone.

Specifically, the second binding agent functions to bind to the target analyte and prevent or significantly slowing its movement. The second binding agent is preferably an antibody but any substance that can bind the target analyte, is suitable. The primary difference between the second binding agent and the first binding agent is that the second binding agent is immobilized to, for example, the polycarbonate member such that the target analyte that flows over or through the polycarbonate can react with the second binding agent to become immobilized there.

Immobilizing the second binding agent can be achieved by a number of methods known to the ordinary skilled artisan. For some membranes and support materials, non-specific absorption is sufficient. For others, and for polycarbonate membranes, the second binding agent can be indirectly immobilized through an intermediary material such as latex particles or derivatized glass particles, which are commercially available. For example, an antibody can coat latex and derivatized particles by non-specific absorption, followed by washing and blocking with a second protein in excess, such as bovine serum albumin. The coated latex or glass beads can then be immobilized within the polycarbonate membrane by applying the latex or glass suspension to the polycarbonate membrane in a solution form.

The collecting portion 148 absorbs excess liquid containing the labeling agent that has not been bound to the second binding agent in the reading portion.

Acceptable carrier liquids include, among others, a buffer solution or a buffer solution with detergent. Buffer solutions neighboring in the pH range of 5–10, and more preferably 6–8 (neighboring neutral pH) and compatible with the labeling agent can be used, such as TRIS, HEPES. Detergent, which is preferably present in the carrier liquid, dissolves in liquid that is added to the sampling device and serves to improve flow as surfactants at one concentration, and if necessary, to solubilize the cell wall or organism for release of antigen or the element to be detected. Several suitable detergents or combination of detergents are known to those skilled in the art and include, nonionic detergents such as TRITON X-100 and NONIDET P40. The concentration of detergent solution varies for each type of detergent and can range from 0.01% to 6%, and preferably from 0.5% to 1.0%.

A target analyte as used herein is any substance that produces or has an antibody, or an antigen, including a microorganism, such as a prokaryotic cell, virus, microplasma or free living eukaryotic cell, protein, or cell metabolite. The target analyte can be introduced by physical contact such as by swabbing a suspected contaminated surface with the device or by introducing the sample in liquid form by, for example, an eye dropper or other dispenser, or by brief immersion of the device in the liquid to be tested.

If wiping or swabbing is carried out, then finger pressure is preferably placed on the bottom layer 130, behind the opening 122 to more fully expose the sample collecting member 160 to the sample.

In operation, the sampling device 100 preferably comes packaged in another sealed container or envelope (not shown). Once the sampling device 100 is taken out, sampling can begin. The collecting member 160 is then exposed to the target area, for instance, by contacting or swabbing the suspected surface, liquid, or other area suspected of containing the analyte with the member 160. Alternatively, the sample to be tested can be directly introduced to the sample collecting member 160. Then, carrier liquid is introduced to the member 160, if needed, to wet the target analyte and move any analyte present to the reading portion. If the target analyte to be tested is in a liquid form, then the carrier liquid may not be necessary, but is preferred.

The applied carrier liquid carrying the sample diffuses through the transfer portion and passes through the labeling portion, which contains luminescent agent attached to a binding agent that is complementary with the target analyte. As the carrier liquid passes therethrough, the liquid releases the labeling agent, which attaches only to the target analyte. The labeled or tagged analyte, along with the excess released labeling agent, now moves into the reading portion 144, which also contains an immobilized binding agent (which could be same as the binding agent in the labeling portion) that is complementary to the target analyte. Here, the binding agent captures the target analyte, which carries the labeling agent, while the non-complementary elements, including excess labeling agent, (excess) pass through the reading zone. The collection portion 148 helps to wick out the excess from the reading portion 144. Whereas the chemiluminescent reaction, as described in the second copending application, provides a spontaneous light emission upon mixing the chemiluminescent reagent with the target analyte, the present luminescent reaction does not produce light until it is first triggered with light exposure. The labeling agent associated with the captured target analyte glows or emits light when exposed to light. The amount of analyte present can be calculated based on the amount of light exposed and collected thereafter. Accordingly, the reading phase can advantageously take place at a later time.

According to the present invention, after a predetermined or desired time lapse, between 2 to 60 minutes, after the sampling, luminescence light produced in response to the presence of target analyte in the sample can be triggered. Devices for detecting intensity of luminescent light (including chemiluminescent, fluorescent or phosphorescent) are generally known. The present interface 1 is adapted to provide a simple way of interfacing the present sampling assay device to such detecting devices. Luminescent light, including phosphorescent and fluorescent light, for instance, can be detected electronically by, for example, luminometer, fluorometer, photomultiplier, photo diode, photofet or charge coupled device. The most preferred is a photomultiplier because of its sensitivity. The interface 1 according to the present invention provides a simple way of interfacing the sampling device 100 to a photomultiplier 50. One known photomultiplier is disclosed in HAMAMATSU PHOTONICS K.K., Photosensor Modules H5773/H5783/H5784 Series, Technical Data, January 1995, the disclosure of which is incorporated herein by reference. The photomultiplier 50 can be, for instance, Module H5773, a schematic functional diagram of which is illustrated in FIG. 2A.

Figure 2:
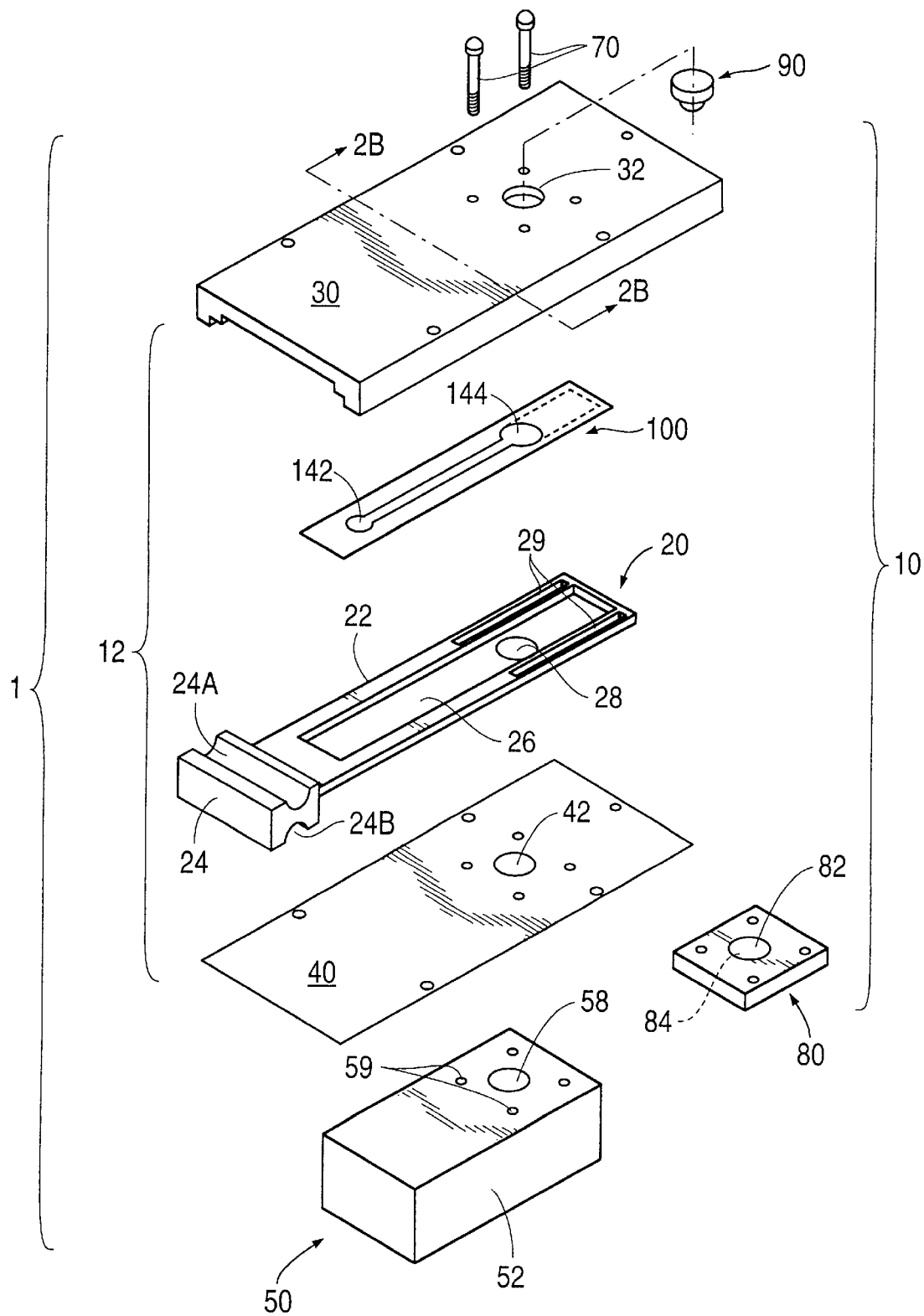
FIG. 2 is an exploded view of a sample interface according to the present invention.
Figure 2A:
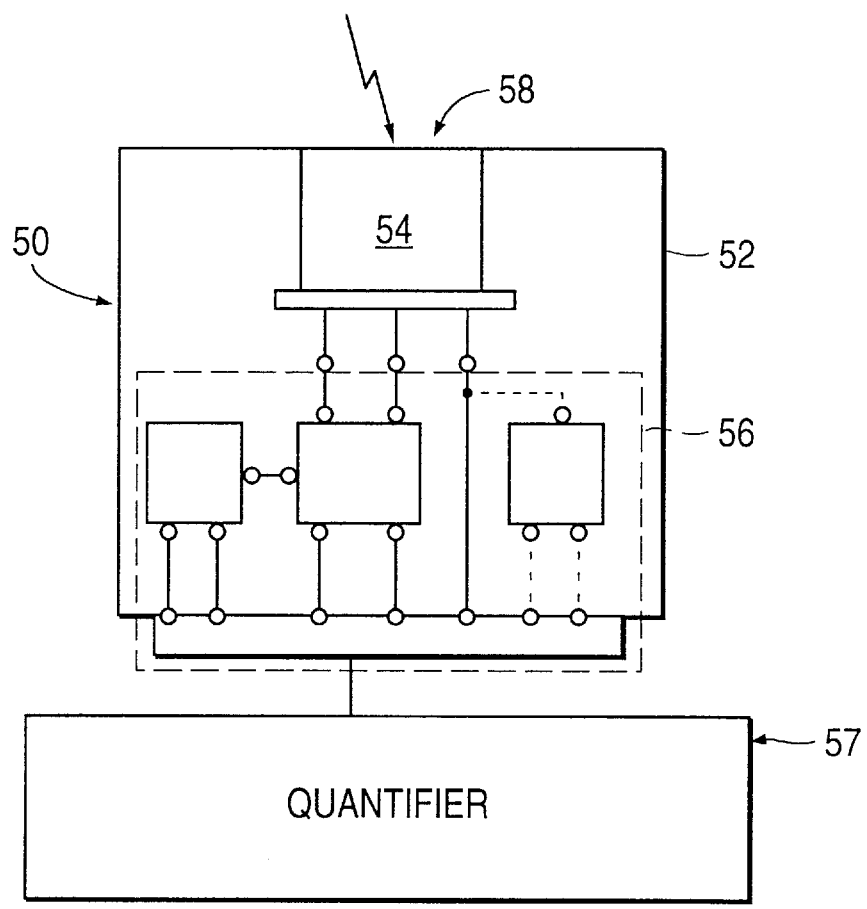
FIG. 2A is a schematic view of a known photodetector connected to a conventional ammeter.

As shown in FIG. 2, the present interface 1 comprises a sampling-device holder 10 connected to a photomultiplier 50. The holder 10 has a housing 12 comprising an enclosure 30 and a base plate 40. The holder also includes a movable tray 20 for seating the sampling device 100. Although FIG. 2 shows the housing 12 in two separate pieces, it could be also formed of a single molded or machined piece, if desired. The tray 20 has a generally flat plate-like body 22 and a handle 24. The flat body 22 has a blind-recess or well 26 (having a bottom) forming a compartment for flatly supporting and seating the sampling device 100. The height or depth of the well is greater than the thickness of the sampling device 100 to maintains the device 100 inside within the well 26 so that no part of the enclosure contacts the device 100. In this regard, a flat sample cover (not shown) can be positioned over the sample to maintain the sampling device in a flat condition. The sample cover should be configured and dimensioned to fit inside the well and placed over at least the reading portion 144. The cover should be shorter than the length of the sampling device 100 so that it does not cover the sampling portion 142 or the reading portion 144. The combined thickness between the cover and the sampling device 100 should not exceed the depth of the well 26.

An opening 28 is formed through the flat body 22 adjacent the distal end of the well 26. When the sampling device is seated in the well and the distal end of the sampling device 100 abuts against the distal end of the well 26, the opening 28 registers in alignment with the reading portion 144 and the bottom-layer opening 132 so that light emitting from the reading portion passes therethrough. The flat body 22 further includes a pair of parallel, longitudinal guiding slots 29, which provide two discrete functions. First, they permit complete passage of fasteners 70, such as bolts or the like, which maintain the present interface 1 together. Second, these slots (with the fasteners acting as a stop) enable the tray to slide by a predetermined length equalling the slot length less the distance between the fasteners passing through the same slot. In other words, the slot limits the movement of the tray, while maintaining the tray connected to the enclosure. The tray thus cannot be pulled out completely without removing the fasteners 70.

The handle 24 has upper and lower contoured recesses 24A, 24B to provide more ergonomical gripping surfaces. The junction at the handle and the flat body preferably should be carefully configured and dimensioned to provide a light-tight seal against the ends of the enclosure 30 and the base plate 40. The tray also serves as a shutter, automatically blocking the photomultiplier reading window 58 when the tray is opened, and opening the reading window 58 when it is closed.

Figure 2B:
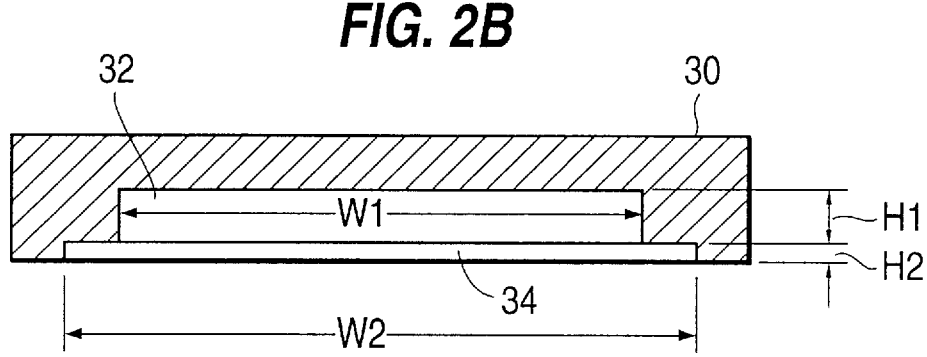
FIG. 2B is a cross-sectional view taken along line 2B—2B of FIG. 2.

FIG. 2B shows a cross-sectional view of the enclosure 30. The base plate 40 and the enclosure 30, which constitute the first and second walls, define a cavity or space to which the tray is inserted. The enclosure is substantially rectangular as shown, although other configurations can be contemplated. The enclosure 30 has a first channel 32 configured and dimensioned to closely fit against the flat body 22. Specifically, the channel 32 has a width W1 and a height H1, substantially the same as the width and height of the flat body 22, only slightly larger to allow the flat body to slide against the side walls of the first channel 32. The tight tolerance is designed to prevent light seepage into the well 26. Alternatively, seals can be placed to block out light. The enclosure also has a second wider channel 34 contiguous with the first channel 32. Specifically, the first channel is above the second channel. This second channel 34 has a second width W2 and a second height H2 (and a length) substantially identical as those of the base plate 40, which occupies the second channel when assembled. Again, a tight tolerance is desirable to prevent light seepage between the enclosure 30 and the base plate 40.

The base plate 40 also has an opening 42, which when assembled with the enclosure 30 and the tray 20, will be in registered alignment with the tray opening 28 to enable light to pass therethrough.

Referring to FIG. 2A, the photomultiplier 50, such as the one disclosed in the aforementioned HAMAMATSU publication, has a housing 52 encasing a phototube 54 and an associated circuitry 56 for outputting a signal correlating to the light intensity detected. The photomultiplier can be connected to a conventional light intensity quantifier 57, such as a KEITHLEY Model 485 Picoammeter (ammeter), which measures low current in the range between 100 fA to 2 mA. The phototube is accessed through the opening 58 formed in the housing 52. The present invention provides a simple, easy to use interface for reading light intensity from the sampling device. The photomultiplier 50, such as the one disclosed in the aforementioned HAMAMATSU publication, has four threaded mounting holes 59. In this regard, the enclosure 30 and the base plate 40 preferably have the same mounting hole pattern for permitting passage of the fasteners 70 (only two shown), such as bolts and screws, so that the holder 10 can be directly mounted to the photomultiplier 50.

The enclosure 30 also has an opening 32 aligned with the base plate opening 42 and the seated reading portion 144. This opening 32 is provided to accommodate a light source 90, such as an LED, a laser diode, a gas-filled light, such as, a Zenon or mercury lamp, connected to a conventional controlling device (not shown), such as a strobe control, and the light detector 50. If the luminescent labeling agent is fluorescent, then the light source is turned on continuously to charge the reading portion from one side, while the light detector 50 reads the amount of light emitted from the reading portion from the opposite side. If the luminescent labeling agent is phosphorescent, then the light source is selectively turned on and off. During the off phase, the reading portion is exposed to the light detector.

Publications by MOLECULAR PROBES, INC. entitled *OPTICAL PROPERTIES OF FLUORESCENT PROBES* and *PHYCOBILIPROTEINS AND THEIR CONJUGATES* disclose certain characteristics of notable examples of fluorescent labeling agents, the disclosures of which are incorporated herein by reference. Specifically, the former publication discloses that a narrow optical bandwidth (<20 nm) is usually used for fluorescence excitation via absorption, whereas the fluorescence detection is much more variable. It also discloses that fluorescence background signal can be minimized by selecting appropriate filters or by selecting a fluorescent probe that absorbs and emits at different (usually longer) wavelengths. The later publication discloses three specific phycobiliproteins (highly soluble fluorescent proteins derived from cyanobacteria and eukaryotic algae) suitable for applications requiring high sensitivity: B-phycoerythrin exhibiting a peak absorption at 546 nm and 565 nm, and a peak emission at 575 nm; R-phycoerythrin proteins exhibiting a peak absorption at 480 nm, 546 nm, and 565 nm, and a peak emission at 578 nm; and Allophycocyanin exhibiting a peak absorption at 650 nm and a peak emission at 660 nm.

One suitable light source 90 for the aforedescribed B-phycoerythrin and R-phycoerythrin proteins and other fluorescent probes is an LED Model 4304H6 (blue light), 4304S5 (green light), and sold by INDUSTRIAL DEVICES, INC., Hackensack, N.J. The 4304H6 LED produces a peak emission at 470 nm, which closely matches the 470 nm peak absorption wavelength of B-phycoerythrin proteins. The 4304S5 LED produces a peak emission at 562 nm, which about matches the 565 nm peak absorption wavelength of R-phycoerythrin. These fluorescent probes can be used as labeling agents with these LEDs in labeling the target analyte. The emission wavelengths from the fluorescent probes are sufficiently separated from the absorption wavelengths. In fluorescent probes, there is no time delay between the excitement and emission phases. That is, the fluorescent probes emit light immediately with the light absorption. When they are not excited, no light is emitted (decays very rapidly for accurate measurements). In this regard, the light source must be on while detecting their emission. Therefore, it is desirable to select a fluorescent agent having the greatest separation between the peak absorption wavelength and the peak emission wavelength, such as R-phycoerythrin proteins, which exhibit a peak absorption at 480 nm (546 nm and 565 nm) and a peak emission at 578 nm. The 546 nm and 565 nm peaks can be filtered out to enhance response. Filters in this regard play an important role in detecting fluorescent light.

A publications by MOLECULAR PROBES, INC. entitled *OPTICAL FILTERS* further discloses some commercially available light sources, such as 365, 405, 435, 545, 575, 615, and 690 nm mercury lamps; 488 and 514 nm argon-ion lasers; 488, 568 and 647 nm argon-krypton lasers; and 543, 594, 633 nm helium-neon lasers. This publication also discloses filters that can be used with known fluorescent agents, the disclosure of which is incorporated herein by reference.

The phosphorescent agents, on the other hand, such as chelated europium or europium compounds, exhibits a time delay between the absorption and emission phases. This delay can be advantageously adapted so that the light measurement is taken while the light source is off. This prevents any possible light contamination from the light source since the reading is taken only when the light source is off. In addition, any background noise attributed to florescent light is also eliminated since it is not active when the light is turned off.

Light generally obeys an inverse square relationship to distance following Lambert's Law. Therefore, if a light detector is used, detection sensitivity is optimized by placing the detector as closely as possible to the reading portion 144. The interface 1 according to the present invention enables that, maximizing the collected light and measurement sensitivity by directly connecting the holder 10 to the photomultiplier 50 to provide a shortest direct optical path. The present inventors have found that the photomultiplier 50, such as the ones disclosed in the aforementioned HAMAMATSU publication has a slight depression around the hole pattern. In this situation, a spacer 80 having an opening 82 in registry with the window 58 and the same bolting pattern can be used. The spacer can also be used to hold an optical filter 84, if it is desired to limit the photomultiplier spectral response. This is particularly useful in blocking out the light from the light source, while permitting the emission to pass through during the fluorescent reading. This spacer 80. however, is only needed when the photomultiplier does not provide a flat planar mounting surface or when a filter 84 is desired to enhance measurement sensitivity.

Photomultiplier, such as the HAMAMATSU Module H5773/H5783/H5784 Series photosensors, have a highest spectral response between 400 and 500 nm, with decreasing responses above and below, but provides spectral response from 185 to 650 nm. Thus, although it would be desirable to select luminescent agent having a peak emission between 400 and 500 nm, the luminescent agent or probe can be detected well outside that range. A filter 84 can also be provided to block out a certain range of spectra to enhance response.

In operation, once the sampling has been made, as described before, the sampling device 100 is positioned on the tray 20, with the distal edge of the device 100 abutting the distal wall of the well 26, where the reading portion will be in registry with the opening 28. Thereafter, the tray is closed, which seals the sampling device against any light seepage, but registering the reading portion with the window opening 58 of the light detector 50 and the light source 90. Any light emitted by the reading portion in response to the labeling agent captured along with the target analyte is measured by the light detector 50. If the measurement is taken immediately after sampling, since it may take time for the analyte to travel to the reading portion, it would be desirable to monitor the reading portion over a predetermined period to observe a peak reading.

If the labeling agent is phosphorescent, such as chelated europium or europium compound, the light source 34 is turned on and off (pulsed) while measurements are being taken between the pulses. The light source charges the labeling agent associated with the target analyte. Then, while the light is in the off phase, the light emitted from the reading portion is read using the light detector 50. A filter 84, which is selected to block the light spectrum from the light source 34, but permit transmission of the light spectrum emitted from the reading portion, can be included in the spacer 80 to enhance response.

If the labeling agent is fluorescent, such as R-phycoerythrin, the light source 34 is turned on while measurements are being taken. The light source charges the labeling agent associated with the target analyte as it is read using the light detector 50. A filter 84, which is selected to block the light spectrum from the light source 34, but permit transmission of the light spectrum emitted from the reading portion, preferably is included in the spacer 80 to filter out noise and enhance response.

In both instances, it would be desirable for the light source 34 to emit a different peak wavelength than the peak labeling emission wavelength to increase reading response. In this regard, it is preferable for the light source to be an LED or a laser diode (as there are a wide variety) emitting at a desired wavelength.

Given the disclosure of the present invention, one versed in the art would readily appreciate that there may be other embodiments and modifications well within the scope and spirit of the present invention. Accordingly, all expedient modifications readily attainable by one versed in the art from the present disclosure within the scope and spirit of the present invention are to be included as further embodiments of the present invention.

Accordingly, the scope of the present invention accordingly is to be defined as set forth in the appended claims.

What is claimed is:

1. An interface for measuring light intensity generated by a sampling device having a reading portion and a sampling portion with means to capture a target analyte labeled with a luminescent agent in the reading portion, comprising:

a) a sample holder comprising:
        a housing having a first wall and a second wall, the first and second walls forming a cavity therebetween, the first wall having a first opening; and
        a tray received in the cavity and movable between an opened position and a closed position, the tray having a compartment adapted to receive and support the sampling device, the tray having a second opening extending through the compartment,
        wherein the second opening is adapted to be in registry with the reading portion when the sampling device is seated in the compartment, wherein the second opening is in registry with the first opening when the tray is in the closed position to enable observation of the reading portion through the first and second openings;
    b) a light detector for converting light emitted from the sampling device to an output signal corresponding to the amount or intensity of the light generated, the light detector having a light gathering window, wherein the light detector is connected to the first wall so that the window is aligned with the first opening; and
    c) a light source connected to the holder and aligned with the first opening to enable light from the light source to reach the reading portion when the sampling device is positioned in the tray.

2. An interface according to claim 1, wherein the second wall has a third opening aligned with the first opening, the light source being seated in the third opening.

3. An interface according to claim 2, wherein the second wall is an enclosure having a channel and the first wall is a base plate connected to the enclosure, the channel defining the cavity.

4. An interface according to claim 3, wherein the tray blocks the first opening when the tray is in the opened position.

5. An interface according to claim 2, wherein the tray includes a handle.

6. An interface according to claim 2, wherein the tray is slidable between the opened and closed positions.

7. An interface according to claim 6, wherein the tray includes a pair of parallel slots, wherein the slots are adapted to be occupied by fasteners spaced along the slots, and wherein the length of the slot less the spacing between the fasteners occupying the same slot defines the amount of the tray sliding movement.

8. An interface according to claim 2, where the light detector is a photomultiplier.

9. An interface according to claim 8, wherein the light source is an LED or a laser diode.

10. An interface according to claim 8, wherein the light source is a gas filled lamp.

11. A system for measuring light intensity generated by a target analyte contained in a sample, comprising:

a) a sampling assay device comprising:
        a container;
        a sampling strip having a sampling portion for receiving a sample, a reading portion for emitting light, and a transfer portion connecting the sampling and reading portions for permitting transfer of the sample from the sampling portion to the reading portion, the sampling strip contained inside the container,
        wherein the reading portion contains a first binding agent complementary to the target analyte to capture the target analyte,
        wherein at least one of the sampling portion and the transfer portion contains a luminescent labeling agent that emits light upon exposure to light and a second binding agent complementary to the target analyte, which second binding agent is bound to the labeling agent, and wherein the container has means to permit introduction of the sample to the sampling portion and a light transmissive portion exposing the reading portion;

b) a sample holder comprising:

a housing having a first wall and a second wall, the first and second walls forming a cavity therebetween, the first wall having a first opening; and a tray received in the cavity and movable between an opened position and a closed position, the tray having a compartment adapted to receive and support the sampling device, the tray having a second opening extending through the compartment, wherein the second opening is in registry with the reading portion when the sampling device is seated in the compartment, wherein the second opening is in registry with the first opening when the tray is in the closed position to enable observation of the reading portion through the first and second openings;

c) a light detector for converting light emitted from the sampling device to an output signal corresponding to the amount or intensity of the light generated, the light detector having a light gathering window, wherein the light detector is connected to the first wall so that the window is aligned with the first opening; and d) a light source connected to the holder and aligned with the first opening to enable light from the light source to reach the reading portion when the sampling device is positioned in the tray; and e) a quantifier for converting the output signal to quantifiable data indicative of the amount of the target analyte.

12. A system according to claims 11, wherein the labeling agent is chelated europium or europium compound and is contained within at least a portion of the transfer portion.

13. A system according to claim 11, wherein the first and second binding agents each are an antigen complementary to the target analyte.

14. A system according to claim 11, wherein the second wall has a third opening aligned with the first opening, the light source being seated in the third opening.

15. A system according to claim 11, wherein the light source is an LED or a laser diode.

16. A system according to claim 11, wherein the sampling strip further includes a collecting portion contiguous with the reading portion for absorbing excess liquid containing the labeling agent not captured along with the target analyte.

17. A system according to claim 16, wherein the sampling strip is made of a material permitting lateral flow of the sample in liquid, wherein at least the reading portion is light transmissive.

18. A system according to claim 16, wherein the collecting portion is made of an adsorbent or absorbent material.

* * * * *